Figure 1:
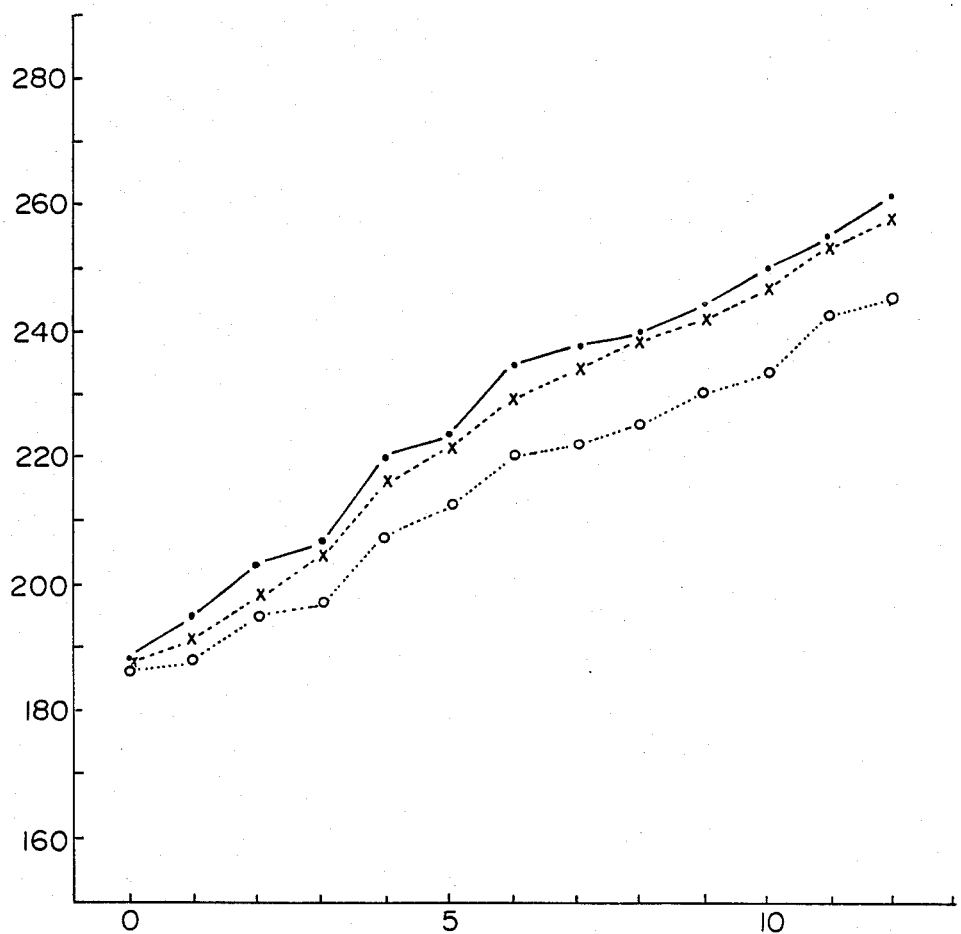

United States Patent [19]

Enomoto et al.

[11] Patent Number: 4,532,238

[45] Date of Patent: Jul. 30, 1985

[54] FINELY PULVERIZED 2,4-DIAMINO-6-(2,5-DICHLORO-PHENYL)-1,3,5-TRIAZINE AND PHARMACEUTICALLY ACCEPTABLE ACID ADDITION SALTS THEREOF

[75] Inventors: Hiroshi Enomoto, Nagaokakyo; Masanobu Kawamata, Kyoto; Akira Nomura, Hirakata; Yoshiaki Aoyagi, Otsu; Fusao Ueda, Shiga, all of Japan

[73] Assignee: Nippon Shinyaku Co., Ltd., Japan

[21] Appl. No.: 403,702

[22] Filed: Jul. 30, 1982

[30] Foreign Application Priority Data

Aug. 4, 1981 [JP] Japan .................. 56-122876

[51] Int. Cl.$^3$ .................. C07D 251/18; A61K 31/53
[52] U.S. Cl. .................. 514/245; 544/206
[58] Field of Search .................. 544/206; 424/249

[56] References Cited

U.S. PATENT DOCUMENTS 3,966,728  6/1976  Murai et al. .................. 544/206

FOREIGN PATENT DOCUMENTS 919103  11/1977  Japan .
1017236  1/1980  Japan .

*Primary Examiner*—John M. Ford
*Attorney, Agent, or Firm*—Jacobs & Jacobs

[57] ABSTRACT

2,4-Diamino-6-(2,5-dichlorophenyl)-1,3,5-triazine and pharmaceutically acceptable acid addition salts thereof in finely pulverized form so that the average particle diameter is 20 microns or less have been found to be particularly useful for the treatment of peptic ulcers.

25 Claims, 1 Drawing Figure

THE AXIS OF ABSCISSA & THE ORDINATE ARE ADMINISTRATION DATES & BODY WEIGHTS, RESPECTIVELY. •——• MEANS CONTROL GROUPS, X------X MEANS FINELY POWDERED GROUPS ACCORDING TO THIS INVENTION, & o-------o MEANS THE ORDINARY CONVENTIONAL POWER GROUPS.

FINELY PULVERIZED 2,4-DIAMINO-6-(2,5-DICHLORO-PHENYL)-1,3,5-TRIAZINE AND PHARMACEUTICALLY ACCEPTABLE ACID ADDITION SALTS THEREOF 2,4-diamino-6-(2,5-dichlorophenyl)-1,3,5-triazine and various acid addition salts thereof are known to exhibit strong anti-ulcer activity (see Japanese Patent Nos. 919103 and 1017236). However, in testing that compound for its anti-ulcer activity, it has been found that disadvantages arise due to lack of reproducibility of the level of anti-ulcer activity when the compound is administered without regard to the average particle size. In particular, it has been found that the compound lacks a dose dependency thereby giving rise to unpredictibility as well as lack of reproducibility of the activity levels.

The present invention is based on the surprising discovery that a number of advantages accrue from finely pulverizing 2,4-diamino-6-(2,5-dichlorophenyl)-1,3,5-triazine or a pharmaceutically acceptable acid addition salt thereof, so that the average particle diameter is 20 microns or less. A particularly useful average particle diameter is 5 to 10 microns and extremely good results have been achieved wherein the average particle diameter is about 8 microns.

When 2,4-diamino-6-(2,5-dichlorophenyl)-1,3,5-triazine or a pharmaceutically acceptable acid addition salt thereof is finely pulverized so that the average particle diameter is 20 microns or less, a number of quite unexpected advantages result. These advantages include a marked improvement in the properties and reproducibility of the activity. For example, the inhibition activity against stress ulcer in rats showed linear dose dependency. In addition, quite surprisingly, investigations on the effect on toxicity revealed that the finely pulverized particles according to the present invention were far less toxic that those of the prior art having an average particle diameter of about 50 microns.

In addition, we have observed that body weight increase inhibition which is a main side effect of administration of the compound of the present invention or a pharmaceutically acceptable acid addition salt thereof, is only transient and moderate and the recovery is far faster than occurs when the prior art having an average particle diameter of about 50 microns is administered.

The present invention, therefore, resides in the discovery of unexpected improvement in properties and decrease in side effects when 2,4-diamino-6-(2,5-dichlorophenyl)-1,3,5-triazine and pharmaceutically acceptable acid addition salts thereof are finely pulverized so that the average particle diameter is 20 microns or less. Also included within the present invention are pharmaceutical compositions useful for treating peptic ulcers in humans and animals which comprises 2,4-diamino-6-(2,5-dichlorophenyl)-1,3,5-triazine or a pharmaceutically acceptable acid addition salt thereof in finely pulverized form so that the average particle diameter is 20 microns or less, preferably 5-10 microns, in combination with a pharmaceutically acceptable carrier. According to a further embodiment of the present invention, the compound may be used in the form of its maleate salt. Both the compound and pharmaceutically acceptable acid addition salts thereof have been found to be particularly useful when the average particle diameter is about 8 microns. Also included within the present invention is the method of treating peptic ulcers in humans and animals which comprises administering to a human or animal in need thereof a therapeutically effective amount of 2,4-diamino-6-(2,5-dichlorophenyl)-1,3,5-triazine or a pharmaceutically acceptable acid addition salt thereof, in finely pulverized form, so that the average particle diameter is 20 microns or less, preferably 5 to 10 microns, in combination with a pharmaceutically acceptable carrier. The compound may be administered as such or in the form of a pharmaceutically acceptable acid addition salt. The maleate salt has been found to be particularly useful. The compounds and the pharmaceutically acceptable acid addition salts thereof, having an average particle diameter of about 8 microns, have been shown to be useful according to the present invention.

The advantages of the present invention are demonstrated when 2,4-diamino-6-(2,5-dichlorophenyl)-1,3,5-triazine is administered orally to rats and its activity on ulcer formation induced by stress is measured by the immobilization-water immersion method. According to that test, when the compound of the present invention is administered, a dosage of 1 mg/kg is effective, whereas when the compound has an average particle diameter of about 50 microns, a dosage of 5 mg/kg was shown to be ineffective. Similar results were obtained using the maleate salt according to the present invention. Table 1 below shows the lack of uniformity of result and linear dose dependency when the compound as known in the art having an average particle diameter of about 50 microns was administered to rats, as above described.

TABLE 1

| Dosages (mg/kg; per os) | Inhibition Rate | | |
| --- | --- | --- | --- |
| 0.37 | 37% | 46% | 29% |
| 1.12 | −9% | 29% | 42% |
| 3.72 | 62% | 47% | 33% |

Since 50 microns is a common particle diameter in pharmaceutical preparations, it was most surprising that such significant and important advantages accrued according to the present invention. Inhibition activity against stress ulcer in rats of the compound and pharmaceutically acceptable acid addition salts in the finely pulverized form of the present invention are set forth in Table 2.

TABLE 2

| | Inhibition Rate | | | | |
| --- | --- | --- | --- | --- | --- |
| | 0.3 | 1.0 | 3.0 | 10 | 30 mg/kg |
| Substance (I) | 33% | 45% | 63% | 70% | 85% |
| Substance (II) | 35% | 51% | 70% | 85% | — |

The data shows linear dose dependency. $ED_{50}$ values can be determined as 1.22 mg/kg (per os) and 0.90 mg/kg (per os), respectively, for substance I - 2,4-diamino-6-(2,5-dichlorophenyl)-1,3,5-triazine and for substance II which is the maleate salt thereof.

It was further quite unexpected to find that when 2,4-diamino-6-(2,5-dichlorophenyl)-1,3,5-triazine having an average particle diameter of about 8 microns was tested for toxicity, that on intraperitoneal injection, no rats were killed with dosages up to 3000 mg/kg while the same compound having an average particle diameter of about 50 microns showed an $LD_{50}$ of 1740 mg/kg (1614 to 1876) when injected intraperitoneally in male rats. A similar effect was observed with the maleate salt according to the present invention. While the $LD_{50}$ of the maleate salt having an average particle diameter of 50 microns was determined to be 495 mg/kg (406 to 604), the maleate salt according to the present invention had an $LD_{50}$ of 835 mg/kg (696 to 1002). This decrease in toxicity is totally unexpected and represents a significant and important advance in the art.

The finely pulverized compound and pharmaceutically acceptable acid addition salts according to the present invention would appear to show decreased toxicity because the mechanism for achieving pharmacological and therapeutic activity and toxicity are quite distinct. The therapeutic results are achieved due to improved absorption, but the side effects most likely result from retention in the digestive tract.

A further advantage results from body weight increase inhibition which is one of the main side effects of the compound and salts of the present invention. When 10 mg/kg or more per day of either the compound or maleate salt is chronically administered to rats orally, body weight increase is inhibited. This is a side effect of triazines of this type. The inhibition is believed to be due to a decrease in food consumption and body weight is generally restored upon cessation of administration of the compound. However, when the compound or a pharmaceutically acceptable acid addition salt thereof according to the present invention having an average particle diameter of about 8 microns was administered, the appearance of the side effect was only transient and moderate and the recovery of body weight was far faster as compared to that occurring when the compound was administered having an average particle diameter of about 50 microns. The improvement was particularly dramatic when the maleate salt according to the present invention was compared with a maleate salt having an average particle diameter of about 50 microns, in accordance with the usual micron size for pharmaceuticals.

FIG. 1 shows a change in body weights which occurs on administration of 15 mg/kg per day to male rats (10 rats in one group) over a continuous 12 day period. The average particle sizes were 8 microns for the compound according to the present invention as compared to the same compound having an average particle diameter of 50 microns.

2,4-diamino-6-(2,5-dichlorophenyl)-1,3,5-triazine and pharmaceutically acceptable acid addition salts thereof may be finely pulverized to achieve the average particle diameter of 20 microns or less by using jet Mill PJM-100NP (Nippon Newmatic MEG Co.). The pulverization is carried out by feeding 2 kg or less of the substance per hour. An average particle diameter of about 8 microns may be prepared in that manner. If necessary, auxiliary pulverizing agents such as starch, anhydrous silicic acid, etc. may be used. In measuring average particle size, the powder is dispersed in physiological saline solution containing one drop of Tween-80 with the aid of an ultrasonic homogenizer for 30 seconds and measured by Coleter Counter TA-II (Coulter Electronics Co., U.S.A.) equipped with aperture tube of 100 microns.

The compound and pharmaceutically acceptable acid addition salts according to the present invention may be formulated into tablets, sugar coated or otherwise, capsules, troches, pills, granules, powders, suppositories, emulsions, suspensions, sirups, and the like, using conventional pharmaceutical techniques. They may be administered one or more daily as needed. Examples of auxiliary materials include:

(1) Fillers and diluents such as starch, lactose, and mannitol (2) Binding agents such as microcrystalline cellulose, methylcellulose, other cellulose derivatives, gum arabic, gelatine, polyethylene glycol, polyvinyl alcohol, and polyvinyl pyrrolidone (3) Wetting agents such as glycerol (4) Disintegrating agents such as carboxylmethyl cellulose (except sodium salt), microcrystalline cellulose, polyethyleneglycol (5) Solubilization retarding agents such as carboxylmethyl cellulose sodium salt (6) Absorption accelerating agents such as quaternary ammonium compounds (7) Surface active agents such as cetyl alcohol, glycerine fatty acid esters (8) Fluidizing agents such as anhydrous silicic acid, synthetic aluminum silicate (9) Lubricants such as talc, magnesium stearate, calcium stearate, solid polyethylene glycol

(10) Coating agents such as AEA (Trademark - Sankyo), MPM (Trademark - Tanabe), shellac, TC-5 (Trademark - Shin-Etsu)

Tablets, sugar coated tablets, capsules, trouches, pills, etc. made from the present invention drugs may contain usual coating agents, etc. which possess untransparent agents therein. Such materials can, for example, be manufactured from polymers or from wax.

The pharmaceutical compositions of the present invention may be formulated into a sustained release form, either by micro-incapsulation or by other techniques known per se in the pharmaceutical industry.

Examples of suitable additives to prepare suppositories are water soluble bases such as polyethylene glycol and oil bases such as cacao butter, Witepsol (Trademark-Dynamite Nobel AG). Such bases may contain surface active agents therein.

Examples of materials used for the manufacture of suspension injections, emulsions, suspensions, sirups, etc. are as follows:

(1) Emulsification and suspensing agents such as water, ethyl alcohol, isopropyl alcohol, ethyl carbonate, benzyl alcohol, benzyl benzoate, propylene glycol, 1,3-butylene glycol, dimethyl formamide, oils/fats, glycol, tetrahydrofurfuryl alcohol, polyethylene glycol (2) Surface active agents such as sorbitan fatty acid esters, polyoxyethylene sorbitan fatty acid esters, polyoxyethylene fatty acid esters, polyoxyethylene ethers of hydrogenated castor oil, lecithine (3) Suspension agents such as carboxymethylcellulose sodium salt, methyl cellulose, other cellulose derivatives, tragacanth, gum arabic, other natural rubbers (4) Preservatives such as para-hydroxybenzoic acid esters, benzalconium chloride, sorbic acid salts The pharmaceutical compositions according to the present invention may also contain the usual coloring agents, preservatives, perfumes, seasoning agents, sweetening agents and the like.

The pharmaceutical compositions according to the present invention contain from about 0.1 to 99.5% and more preferably from about 0.5 to 95% of 2,4-diamino-6-(2,5-dichlorophenyl)-1,3,5-triazine or a pharmaceutically acceptable acid addition salt thereof.

In the compositions according to the present invention, the compound or pharmaceutically acceptable acid addition salt thereof may be the sole therapeutic agent or the composition may contain other therapeutic agents such as digestive enzymes, antacids, inhibitants for stomach secretion, aromatic stomach agents, bitter stomach agents, protective agents for stomach mucous, anti-cholinic agents and the like. The compositions of the present invention may also contain anti-inflammatory agents.

The route of administration is generally oral, but other routes such as rectal administration is also suitable. Generally the daily dosage will be from about 0.5 to 100 mg/kg but the precise dosage may vary according to the severity of the condition, the degree of symptoms, the past medical history of the patient and the like. When a larger amount is administered, it is generally desirable to divide the same into individual dosages.

The following non-limitative example more particularly illustrates the present invention:

EXAMPLE 2,4-Diamino-6-(2,5-dichlorophenyl)-1,3,5-triazine is powdered by supplying it at rate of not more than 2 kg/hour to a Jet Mill PJM-100 NP (Nippon Newmatic Mfg Co). The pulverized pharmaceutical is dispersed in a physiological saline solution containing one drop of Tween-80 by the use of ultrasonic homogenizer for 30 seconds and their particle diameter in average is measured by Coulter Counter TA-II (Coleter Electronics Co, U.S.A.) and the result is about 8 microns.

What is claimed is:

1. A composition of matter consisting essentially of 2,4-diamino-6-(2,5-dichlorophenyl)-1,3,5-triazine or a pharmaceutically acceptable acid addition salt thereof in finely pulverized form so that the average particle diameter is 20 microns or less.

2. A composition according to claim 1 in the form of the maleate salt.

3. The composition according to claim 1 wherein the average particle diameter is 5 to 10 microns.

4. A composition according to claim 2 wherein the average particle diameter is 5 to 10 microns.

5. A composition according to claim 1 wherein the average particle diameter is about 8 microns.

6. A composition according to claim 2 wherein the average particle diameter is about 8 microns.

7. A composition according to claim 1 wherein the 2,4-diamino-6-(2,5-dichlorophenyl)-1,3,5-triazine has an average particle diameter of about 8 microns.

8. A pharmaceutical composition useful for the treatment of peptic ulcers in humans and animals which comprises a therapeutically effective amount of 2,4-diamino-6-(2,5-dichlorophenyl)-1,3,5-triazine or a pharmaceutically acceptable acid addition salt thereof in finely pulverized form so that the average particle diameter is 20 microns or less, in combination with a pharmaceutically acceptable carrier.

9. A composition according to claim 8 wherein the compound is in the form of the maleate salt.

10. A composition according to claim 8 wherein the average particle diameter is 5 to 10 microns.

11. A composition according to claim 9 wherein the average particle diameter is 5 to 10 microns.

12. A composition according to claim 8 wherein the average particle diameter is about 8 microns.

13. A composition according to claim 9 wherein the average particle diameter is about 8 microns.

14. A composition according to claim 8 wherein the compound is 2,4-diamino-6-(2,5-dichlorophenyl)-1,3,5-triazine and the average particle diameter is about 8 microns.

15. A composition according to claim 8 in oral administration form.

16. A composition according to claim 8 in rectal administration form.

17. A method of treating peptic ulcers in humans and animals which comprises administering to a human or animal in need thereof a therapeutically effective amount of 2,4-diamino-6-(2,5-dichlorophenyl)-1,3,5-triazine or a pharmaceutically acceptable acid addition salt thereof in finely pulverized form so that the average particle diameter is 20 microns or less, in combination with a pharmaceutically acceptable carrier.

18. A method according to claim 17 wherein the compound is in the form of the maleate salt.

19. A method according to claim 17 wherein the average particle diameter is 5 to 10 microns.

20. A method according to claim 18 wherein the average particle diameter is 5 to 10 microns.

21. A method according to claim 17 wherein the average particle diameter is about 8 microns.

22. A method according to claim 18 wherein the average particle diameter is about 8 microns.

23. A method according to claim 17 wherein the compound is 2,4-diamino-6-(2,5-dichlorophenyl)-1,3,5-triazine and the average particle diameter is about 8 microns.

24. A method according to claim 17 wherein the administration is oral.

25. A method according to claim 17 wherein the administration is rectal.

* * * * *